(12) United States Patent
Serno et al.

(10) Patent No.: US 8,841,446 B2
(45) Date of Patent: Sep. 23, 2014

(54) MEDICAMENTS CONTAINING VARDENAFIL HYDROCHLORIDE TRIHYDRATE

(71) Applicant: Bayer Intellectual Property GmbH, Monheim (DE)

(72) Inventors: Peter Serno, Gladbach (DE); Alfons Grunenberg, Dormagen (DE); Andreas Ohm, Neuss (DE); Rainer Bellinghausen, Odenthal (DE); Elmer Vollers, Leverkusen (DE); Jan-Olav Henck, Willich (DE)

(73) Assignee: Bayer Intellectual Property GmbH, Monheim (DE)

( * ) Notice: Subject to any disclaimer, the term of this patent is extended or adjusted under 35 U.S.C. 154(b) by 0 days.

(21) Appl. No.: 13/625,481

(22) Filed: Sep. 24, 2012

(65) Prior Publication Data

US 2013/0078306 A1   Mar. 28, 2013

Related U.S. Application Data

(63) Continuation of application No. 10/521,534, filed as application No. PCT/EP03/07093 on Jul. 3, 2003, now Pat. No. 8,273,876.

(30) Foreign Application Priority Data

Jul. 16, 2002   (DE) .................................. 102 32 113

(51) Int. Cl.
*A61K 31/53*    (2006.01)
*A61P 15/10*    (2006.01)
*A61K 9/28*     (2006.01)
*C07D 487/04*   (2006.01)
*A61K 9/20*     (2006.01)

(52) U.S. Cl.
CPC . *A61K 31/53* (2013.01); *A61K 9/28* (2013.01); *A61K 9/2866* (2013.01); *C07D 487/04* (2013.01); *A61K 9/2893* (2013.01); *A61K 9/2095* (2013.01)
USPC ......................................... 544/184; 514/243

(58) Field of Classification Search
None
See application file for complete search history.

(56) References Cited

U.S. PATENT DOCUMENTS

| | | | |
|---|---|---|---|
| 2,705,715 A | 4/1955 | Baker et al. | |
| 3,036,070 A | 5/1962 | Druey et al. | |
| 3,169,129 A | 2/1965 | Rodgers et al. | |
| 3,331,840 A | 7/1967 | Fry et al. | |
| 3,333,961 A | 8/1967 | Fry et al. | |
| RE26,565 E | 4/1969 | Rodgers et al. | |
| 3,840,537 A | 10/1974 | Garside et al. | |
| 3,941,785 A | 3/1976 | Clarke et al. | |
| 4,039,544 A | 8/1977 | Broughton et al. | |
| 4,052,390 A | 10/1977 | Broughton et al. | |
| 4,060,615 A | 11/1977 | Matier et al. | |
| 4,159,330 A | 6/1979 | Doria et al. | |
| 4,167,568 A | 9/1979 | Knowles et al. | |
| 4,278,673 A | 7/1981 | Hartley et al. | |
| 4,379,788 A | 4/1983 | Heider et al. | |
| 4,431,440 A | 2/1984 | Bhalla et al. | |
| 4,666,908 A | 5/1987 | Hamilton | |
| 4,885,301 A | 12/1989 | Coates | |
| 4,923,874 A | 5/1990 | McMahon et al. | |
| 5,047,404 A | 9/1991 | Coates et al. | |
| 5,073,559 A | 12/1991 | Coates | |
| 5,075,310 A | 12/1991 | Coates et al. | |
| 5,147,875 A | 9/1992 | Coates et al. | |
| 5,250,534 A | 10/1993 | Bell et al. | |
| 5,254,571 A | 10/1993 | Coates et al. | |
| 5,272,147 A | 12/1993 | Bell et al. | |
| 5,294,612 A | 3/1994 | Bacon et al. | |
| 5,316,906 A | 5/1994 | Haugland et al. | |
| 5,346,901 A | 9/1994 | Bell et al. | |
| 5,426,107 A | 6/1995 | Bell et al. | |
| 5,482,941 A | 1/1996 | Terrett | |
| 5,545,738 A * | 8/1996 | Borrega et al. ............... | 544/291 |
| 5,552,152 A | 9/1996 | Shen | |
| 5,591,742 A | 1/1997 | Bell et al. | |
| 5,719,283 A | 2/1998 | Bell et al. | |
| 5,734,053 A | 3/1998 | Terrett | |
| 6,100,270 A | 8/2000 | Campbell | |
| 6,465,010 B1 | 10/2002 | Lagoviyer et al. | |
| 6,566,360 B1 | 5/2003 | Niewohner et al. | |
| 6,890,922 B2 | 5/2005 | Niewohner et al. | |
| 7,067,149 B1 | 6/2006 | Chauveau et al. | |
| 7,122,540 B2 | 10/2006 | Niewohner et al. | |

(Continued)

FOREIGN PATENT DOCUMENTS

BE   865125 A1   9/1978
DE   2255172 A1   5/1973

(Continued)

OTHER PUBLICATIONS

Specification and Pending Claims of Co-Pending U.S. Appl. No. 12/569,720.

(Continued)

*Primary Examiner* — Bethany Barham
*Assistant Examiner* — Randeep Singh
(74) *Attorney, Agent, or Firm* — Edwards Wildman Palmer LLP; Ralph A. Loren; Nicholas J. DiCeglie, Jr.

(57) ABSTRACT

The invention relates to a method for producing medicaments that contain vardenafil hydrochloride, essentially as trihydrate in solid form, and to medicaments that can be obtained according to this method.

15 Claims, 9 Drawing Sheets

(56) References Cited

U.S. PATENT DOCUMENTS

| | | | |
|---|---|---|---|
| 7,314,871 | B2 | 1/2008 | Niewohner et al. |
| 7,695,735 | B2 | 4/2010 | Chauveau et al. |
| 8,263,126 | B2 | 9/2012 | Oury et al. |
| 2002/0119195 | A1 | 8/2002 | Sen et al. |
| 2004/0043996 | A1 | 3/2004 | Nadkarni |
| 2004/0109890 | A1 | 6/2004 | Sugimoto et al. |
| 2004/0152700 | A1 | 8/2004 | Niewohner et al. |
| 2004/0265380 | A1 | 12/2004 | Delmas et al. |
| 2005/0019391 | A1 | 1/2005 | Gendrot et al. |
| 2006/0078614 | A1 | 4/2006 | Venkatesh |
| 2006/0111354 | A1 | 5/2006 | Serno et al. |
| 2006/0177508 | A1 | 8/2006 | Chauveau et al. |
| 2007/0036861 | A1 | 2/2007 | Oury et al. |

FOREIGN PATENT DOCUMENTS

| | | | |
|---|---|---|---|
| DE | 2364076 | A1 | 7/1974 |
| DE | 2811780 | A1 | 9/1978 |
| DE | 19812462 | A1 | 9/1999 |
| DE | 10232113 | | 1/2004 |
| EP | 0009384 | A1 | 4/1980 |
| EP | 0162715 | A2 | 11/1985 |
| EP | 0201188 | A2 | 12/1986 |
| EP | 0293063 | A1 | 11/1988 |
| EP | 0347146 | A2 | 12/1989 |
| EP | 0349239 | A2 | 1/1990 |
| EP | 0351058 | A1 | 1/1990 |
| EP | 0352960 | A2 | 1/1990 |
| EP | 0371731 | A2 | 6/1990 |
| EP | 0442204 | A2 | 8/1991 |
| EP | 0463756 | A1 | 1/1992 |
| EP | 0526004 | A1 | 2/1993 |
| EP | 0636626 | A1 | 2/1995 |
| EP | 0669324 | A1 | 8/1995 |
| EP | 0702555 | A1 | 3/1996 |
| EP | 0812845 | A1 | 12/1997 |
| EP | 960621 | A2 | 12/1999 |
| EP | 1120120 | A1 | 8/2001 |
| EP | 1413294 | A1 | 4/2004 |
| GB | 1338235 | A | 11/1973 |
| GB | 1584461 | A | 2/1981 |
| WO | WO-9306104 | A1 | 4/1993 |
| WO | WO-9307149 | A1 | 4/1993 |
| WO | WO-9312095 | A1 | 6/1993 |
| WO | WO-93/23017 | | 11/1993 |
| WO | WO-9400453 | A1 | 1/1994 |
| WO | WO-9405661 | A1 | 3/1994 |
| WO | WO-9428902 | A1 | 12/1994 |
| WO | WO-9429277 | A1 | 12/1994 |
| WO | WO-9616657 | A1 | 6/1996 |
| WO | WO-9703675 | | 2/1997 |
| WO | WO-9924433 | A1 | 5/1999 |
| WO | WO-0020033 | A1 | 4/2000 |
| WO | WO-0027357 | A1 | 5/2000 |
| WO | WO-00/42992 | | 7/2000 |
| WO | WO-0057857 | A1 | 10/2000 |
| WO | WO-01/27101 | A2 | 4/2001 |
| WO | WO-01/47928 | A2 | 7/2001 |
| WO | WO-0205820 | A1 | 1/2002 |
| WO | WO-02/09713 | A2 | 2/2002 |
| WO | WO-0247607 | A2 | 6/2002 |
| WO | WO-02062315 | A1 | 8/2002 |
| WO | WO-02085336 | A1 | 10/2002 |
| WO | WO-02092057 | A1 | 11/2002 |
| WO | WO-03039520 | A1 | 5/2003 |
| WO | WO-03/051338 | | 6/2003 |
| WO | WO-03/051338 | A1 | 6/2003 |
| WO | WO-03051338 | A1 | 6/2003 |
| WO | WO-03072084 | A1 | 9/2003 |
| WO | WO-2004006894 | A1 | 1/2004 |
| WO | WO-2004/012702 | | 2/2004 |
| WO | WO-2004/012702 | A1 | 2/2004 |
| WO | WO-2004017976 | A1 | 3/2004 |
| WO | WO-2004110411 | A2 | 12/2004 |
| WO | WO-2005037319 | A1 | 4/2005 |
| WO | WO-2005/110419 | | 11/2005 |
| WO | WO-2005/110419 | A1 | 11/2005 |
| WO | WO-2006047493 | A2 | 5/2006 |
| WO | WO-2006055142 | A2 | 5/2006 |
| WO | WO-2006058250 | A2 | 6/2006 |
| WO | WO-2006/092207 | | 9/2006 |
| WO | WO-2007002125 | A1 | 1/2007 |
| WO | WO-2007029376 | A1 | 3/2007 |

OTHER PUBLICATIONS

Baratti, C.M., et al: "Effects of sildenafil on long-term retention of an inhibitory avoidance response in mice," Behavioural Pharmacology, England, Dec. 1999, vol. 10, No. 8, pp. 731-737.

Schultheiss, D., et al: "Cognitive Side Effects of Sildenafil: An Assessment Using Event-Related Brain Potentials," European Urology, vol. 37, No. suppl. 2, Mar. 2000, p. 82.

Giuliano, F., et al: "Comparative Study of the Facilitator Proerectile Effect of Vardenafil and Sildenafil in Anaesthetised Rats," European Urology, vol. suppl. 5, No. 39, p. 108.

Sybertz, E., et al: "Inhibitors of PDE1 and PDE5 cGMP phospodiesterases: patents and therapeutic potential," Expert Opinion on Therapeutic Patents, Ashley Publications, vol. 7, No. 6, 1997, pp. 631-639.

Ahn, H.S., et al.: "Calcium-Calmodulin-Stimulated and Cyclic-GMP-Specific Phosphodiesterases", Advances in Second Messenger and Phosphoprotein Research, 25: 271-283 (1992).

Aronson, W.J., et al.: "The Role of Nitric Oxide and Cyclic GMP in Mediating Pelvic Nerve Stimulation Induced Erection in Dogs", J. Urology, 147: 454A (1992).

Azadzoi, K.M., et al: "Diabetes Mellitus Impairs Neurogenic and Endothelium-Dependent Relaxation of Rabbit Corpus Cavernosum Smooth Muscle", J. Urol., 148: 1587-1591 (Nov. 1992).

Azadzoi, K.M., et al.: "Endothelium-Derived Nitric Oxide and Cyclooxygenase Products Modulate Corpus Cavernosum Smooth Muscle Tone", J. Urol. 147: 220-225 (Jan. 1992).

Azadzoi, K.M. et al.: "Hypercholesterolemia Impairs Endothelium-Dependent Relaxation of Rabbit Corpus Cavernosum Smooth Muscle", J. Urol. 146: 238-240 (Jul. 1991).

Beavo, J.A., "Cyclic Nucleotide Phosphodiesterases: Functional Implications of Multiple Isoforms", Physiological Reviews, 75(4): 725-748 (Oct. 1995).

Beavo, J.A., et al.: "Multiple Cyclic Nucleotide Phosphodiesterase", Mol. Pharmacol. 46: 399-405 (1994).

Beavo, J.A., et al.: "Primary sequence of cyclic nucleotide phosphodiesterase isozymes and the design of selective inhibitors", TIPS, 11: 150-155 (Apr. 1990).

Bowman, A., et al.: "Cyclic GMP mediates neurogenic relaxation in the bovine retractor penis muscle", Br. J. Pharmac. 81: 665-674 (1984).

Burger, A., Med. Chem., 2nd ed., Interscience Publishers, Inc., New York (1960), "Relation of Chemical Structure and Biological Activity", pp. 36-45.

Bush, M.A., PhD Thesis, University of California, Los Angeles (1993), "The Role of the L-Arginine-Nitric Oxide-Cyclic GMP Pathway in Relaxation of Corpus Cavernosum Smooth Muscle".

Bush, P.A., et al.: "Biosynthesis of Nitric Oxide and Citrulline from L-Arginine by Constitutive Nitric Oxide Synthase Present in Rabbit Corpus Cavernosum", Biochem. & Biophys. Res. Comm. 186(1): 308-314 (Jul. 1992).

Bush, P.A. et al.: "Comparison of nonadrenergic, noncholingergic- and nitric oxide-mediated relaxation of corpus cavernosum", Int. J. Impotence Res. 4:85-93 (1992).

Bush, P.A.: "Nitric Oxide is a Potent Relaxant of Human and Rabbit Corpus Cavernosum", J. Urology, 147: 1650-1655 (Jun. 1992).

Coste, H., et al.: "Characterization of a Novel Potent and Specific Inhibitor of Type V Phosphodiesterase", Biochemical Pharmacology 50(10): 1577-1585 (1995).

Dumaitre, B., et al.: "Synthesis and Cyclic GMP Phosphodiesterase Inhibitory Activity of a Series of 6-Phenylpyrazolo[3,4-d]pyrimidones", J. Med. Chem. 39: 1635-1644 (1996).

(56) References Cited

OTHER PUBLICATIONS

Goodman and Gilman's, The Pharmacological Basis of Therapeutics, Ed. Gilman, et al., McGraw Hill, 8th Ed., (1990), pp. 33-43.
Hamilton, H.W., et al.: "Synthesis and Structure—Activity Relationships of Pyrazolo[4,3-d]pyrimidin-7-ones as Adenosine Receptor Antagonists", J. Med. Chem. 30: 91-96 (1987).
Holmquist, F., et al: "Actions of 3-Morpholinosydnonimin (SIN-1) on Rabbit Isolated Penile Erectile Tissue", J. Urology, 150: 1310-1315 (Oct. 1993).
Holmquist, F., et al.: "Effects of the Nitric Oxide Synthase Inhibitor NG Nitro-L-Arginine on the Erectile Response to Cavernosum Nerve Stimulation in the Rabbit", Acta Physiol. Scand. 143: 299-204 (1991).
Ignarro, L. J., et al.: "Neurotransmitter Identity Doubt", Nature 347: 131 (Sep. 1990).
Ignarro, L. J., et al.: "Nitric Oxide and Cyclic GMP Formation Upon Electrical Field Stimulation Cause Relaxation of Corpus Cavernosum Smooth Muscle", Biochem. & Biophys. Res. Comm. 170(2): 843-850 (Jul. 1990).
Kim, N., et al.: "Oxygen Tension Regulates the Nitric Oxide Pathway. Physiological Role in Penile Erection", J. Clin. Invest. 91: 437-442 (Feb. 1993).
Kim, N., et al.: A Nitric Oxide-like Factor Mediates Nonadrenergic-Noncholinergic Neurogenic Relaxation of Penile Corpus Cavernosum Smooth Muscle, J. Clin. Inv. 88: 112-118 (Jul. 1991).
Korenman, S.G., et al.: "Treatment of Vasculogenic Sexual Dysfunction with Pentoxifylline", JAGS 41(4): 363-366 (Apr. 1993).
Lee, S.J., et al.: "Discovery of Potent Cyclic GMP Phosphodiesterase Inhibitors. 2-Pyridyl- and 2-Imidazolylquinazolines Possessing Cyclic GMP Phosphodieterase and Thromboxane Synthesis Inhibitory Activities", J. Med. Chem. 38: 3547-3557 (1995).
Morrison, R.T., et al.: Organic Chemistry, Allyn and Bacon, Inc., 3rd ed., (1972), pp. 858-859.
Murray, K.J.: Phosphodiesterase V Inhibitors, DN&P, 6(3): 150-156 (Apr. 1993).
Nicholson, C.D., et al.: "Differential modulation of tissue function and therapeutic potential of selective inhibitors of cyclic nucleotide phosphodiesterase isoenzymes", TIPS, 12: 19-27 (Jan. 1991).
Rajfer, J., et al.: Nitric Oxide as a Mediator of Relaxation of the Corpus Cavernosum in Response to Nonadrenergic, Noncholinergic Neurotransmission, The New England Journal of Medicine, 326(2): 90-94 (Jan. 1992).
Saenz De Tejada, I., et al.: Cholinergic Neurotransmission in Human Corpus Cavernosum. I. Responses of Isolated Tissue, Am. J. Physiol., 254: H459-H467 (1988).
Saenz De Tejada, I., et al.: "Impaired Neurogenic and Endothelium-Mediated Relaxation of Penile Smooth Muscle from Diabetic Men with Impotence", N. Engl. J. Med. 320: 1025-1030 (Apr. 1989).
Silver, P.J., et al.: "Cyclic GMP Potentation by WIN 58237, a Novel Cyclic Nucleotide Phosphodiesterase Inhibitor", Journal of Pharmacology and Experimental Therapeutics 271(3): 1143-1149 (1994).
Stief, C.G., et al.: Cyclic Nucleotide Phosphodiesterase (PDE) Isoenzymes in Human Cavernous Smooth Muscle: Characterization and Functional Effects of PDE-Inhibitors in Vitro and in Vivo, Int. J. Impot. Res. 7(1): 03 (Sep. 1995).
Sybertz, E.J., et al.: "cGMP Phosphodiesterase Inhibition: A New Mechanism for the Discovery of Therapeutic Agents", Current Pharma. Design 1(4): 373-390 (1995).
Taher, A., et al.: Cyclic Nucleotide Phosphodieterase in Human Cavernous Smooth Muscle, World J. Urol., 15: 32-35 (1997).
Taher, A., et al.: Phosphodiesterase Activity in Human Cavernous Tissue and the Effect of Various Selective Inhibitors, J. Urology 149(4): 285 (Apr. 1993).
Taher, A., et al.: "Cyclic nucleotide phosphodiesterase activity in human cavernous smooth muscle and the effect of various selective inhibitors", Int. J. Impotence Res. 4(2): 11 (1992).
Takase, Y., et al: "The Quinazoline Derivatives as Novel Potent and Selective Inhibitors of Cyclic GMP-Phosphodiesterase", 206th American Chemical Society National Meeting, Chicago (1993).
Terret, N.K., et al.: "Sildenafil (Viagra™), a Potent and Selective Inhibitor of Type 5 CGMP Phosphodiesterase with Utility for the Treatment of Male Erectile Dysfunction", Biorg. & Med. Chem. Letters 6(15): 1819-1824 (1996).
Thompson, W.J.: "Cyclic Nucleotide Phosphodiesterases: Pharmacology, Biochemistry and Function", Pharmac. Ther. 5: 13-33 (1991).
Torphy, T.J., et al.: "Characterization and Selective Inhibition of Cyclic Nucleotide Phosphodiesterase Isozymes in Canine Tracheal Smooth Muscle", Molecular Pharmacology 37: 206-214 (1989).
Trapani, A.J., et al.: "Hemodynamic Basis for the Depressor Activity of Zaprinast, a Selective Cyclic GMP Phosphodiesterase Inhibitor", J. Pharmacol. & Exp. Ther. 258: 269-274 (1991).
Trigo-Rocha, F., et al.: The effect of intracavernous injection of potassium channel openers in monkeys and dogs, Int. J. Impotence Res. 7: 41-48 (1995).
Trigo-Rocha, F., et al.: "The Role of Cyclic Adenosine Monophosphate, Cyclic Guanosine Monophosphate, Endothelium and Nonadrenergic, Noncholinergic Neurotransmission in Canine Penile Erection", J. Urology 149: 872-887 (Apr. 1993).
Trigo-Rocha, F., et al.: "Nitric oxide and cGMP: mediators of pelvic nerve-stimulated erection in dogs", J. Am. Phys. 264(2): H419-H422 (Feb. 1993).
Trigo-Rocha, F., et al.: "Intracellular Mechanism of Penile Erection in Monkeys", Neurology and Urodynamics 13: 71-80 (1994).
Chem. Abstr. 87: 201571g (1977), Koizumi, M., et al.: "4(3H)-Quinazolines", Chugai Pharmaceutical Co., Ltd., Japan. Kokai, JP 52051378.
Draber, W., et al.: "Rational Approaches to Structure, Activity, and Ecotoxicology of Agrochemicals", CRC Press, Boca Raton, (1992) p. 4.
Korolkovas, A.: Essentials of Medicinal Chemistry, 2nd Edition, John Wiley & Sons, New York (1988), pp. 78-82.
Gibson, A.: "Phosphodiesterase 5 Inhibitors and Nitrergic Transmission—From Zaprinast to Sildenafil", Eur. J. Pharmacol. 411: 1-10 (2001).
Katz, et al.: Am. Coll. Cardiol. 36(3): 845-851 (2000).
Charles, I., et al.: "Bicyclic Heterocycles with Nitrogen at the Ring Junction. Part 2. Application of the Dakin-West Reaction to the Synthesis of Imidazo-[5,1-f]-1,2,4-triazin-4(3H)-ones", J. Chem. Soc., Perkin Transactions 1, No. 5, pp. 1139-1146 (May 1980).
Notice of Opposition issued in European Patent No. EP 1858490, by Generics [UK] Limited, dated Jan. 11, 2013.
Notice of Opposition issued in European Patent No. EP 1858490, by Accord Healthcare, dated Jan. 11, 2013.
Fu et al., "Orally fast disintegrating tablets", Critical Reviews in Therapeutic Drug Carrier systems, 21(6); 433-475 (2004).
Compositions of Pharmaburst® B1, B2 and C1, published Apr. 20, 2004.

* cited by examiner

Figure 2: Raman spectrum of vardenafil HCl 3 H₂O
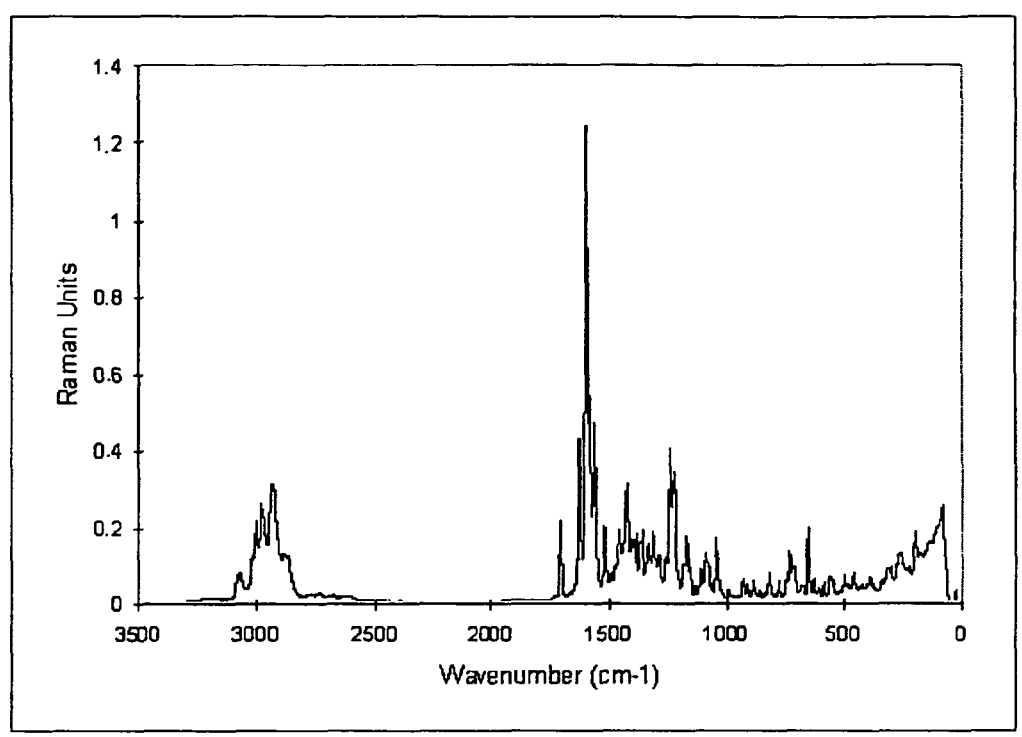

Figure 3: Detection of the trihydrate form of vardenafil HCl in 20mg tablet
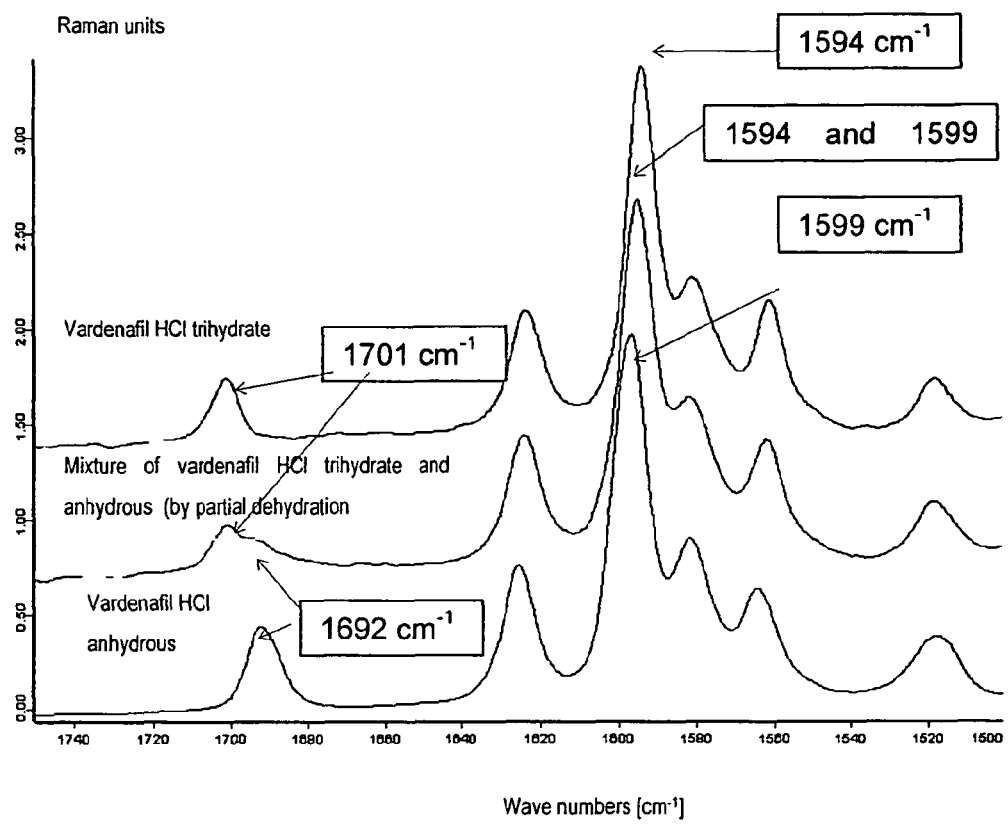

Figure 4: IR spectrum of vardenafil HCl 3 H$_2$O
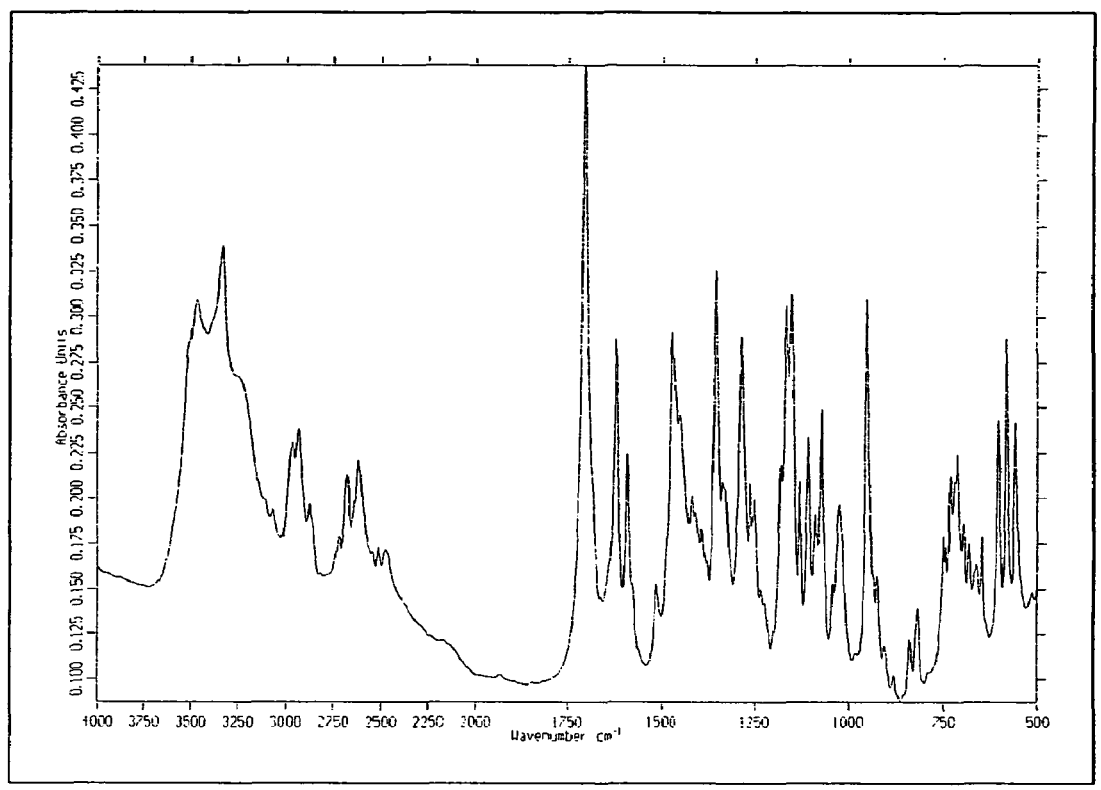

Figure 5: NIR spectrum of vardenafil HCl 3 H₂O
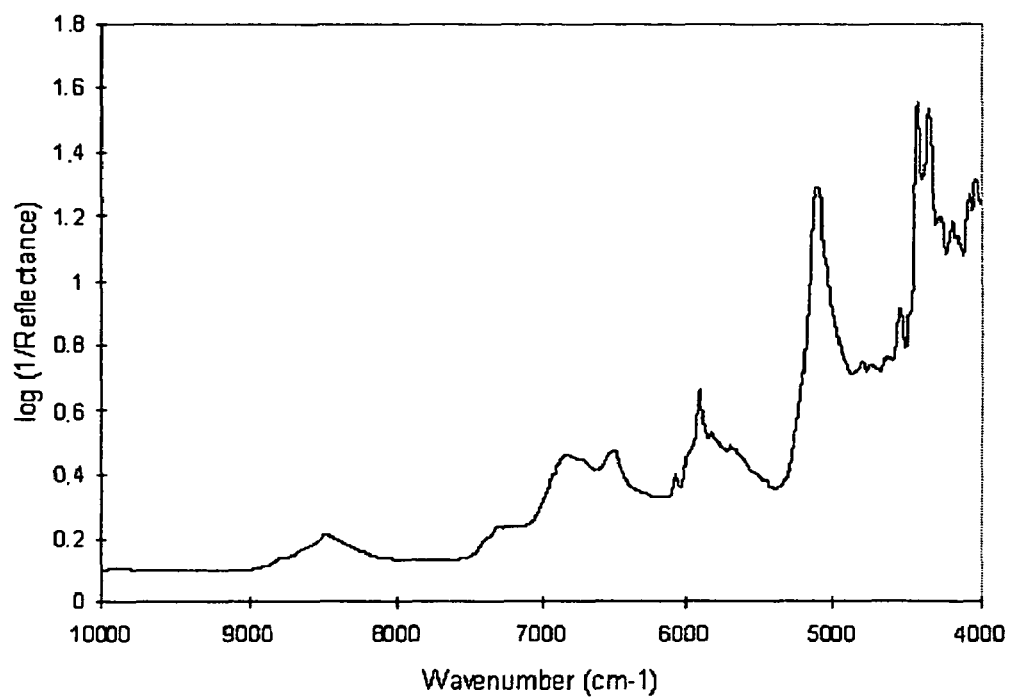

Figure 6: FIR spectrum of vardenafil HCl 3 H$_2$O
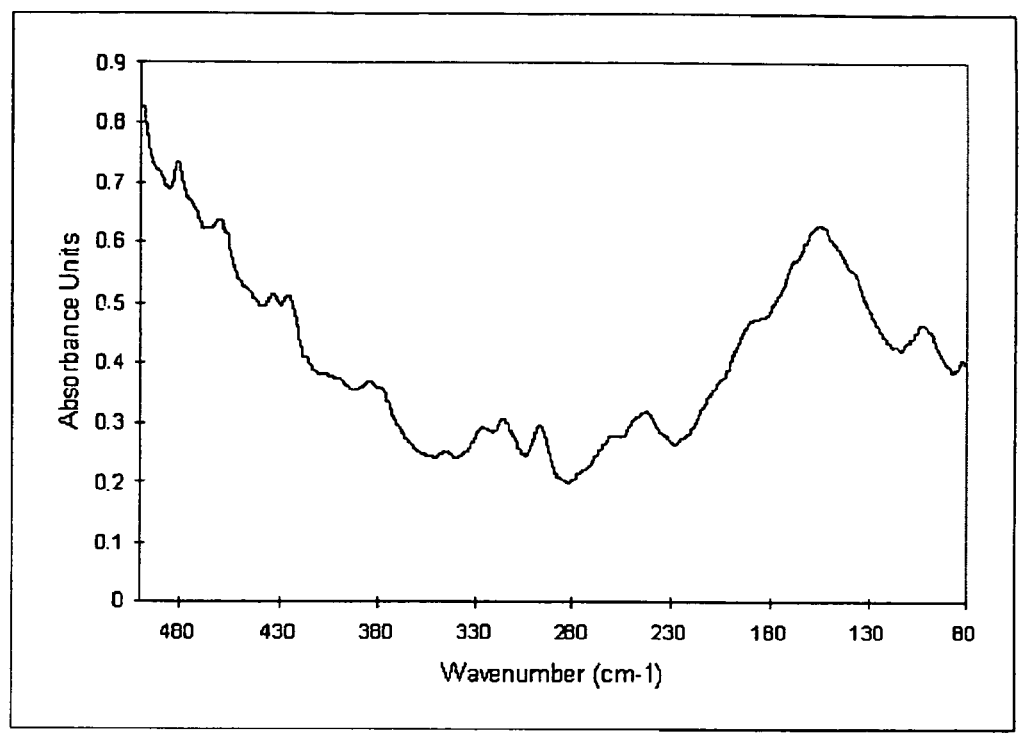

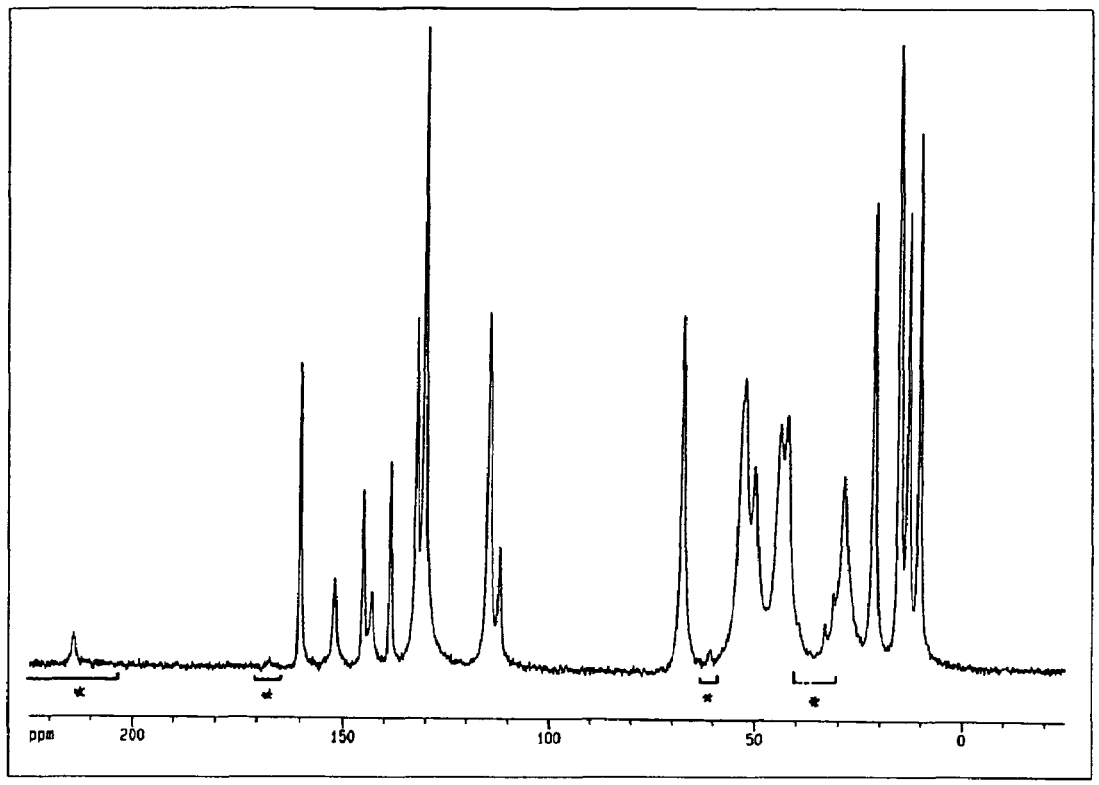
Figure 7: $^{13}$C solid NMR spectrum of of vardenafil HCl 3 H$_2$O

Figure 8: X-ray diffractogram of vardenafil HCl 3 H₂O
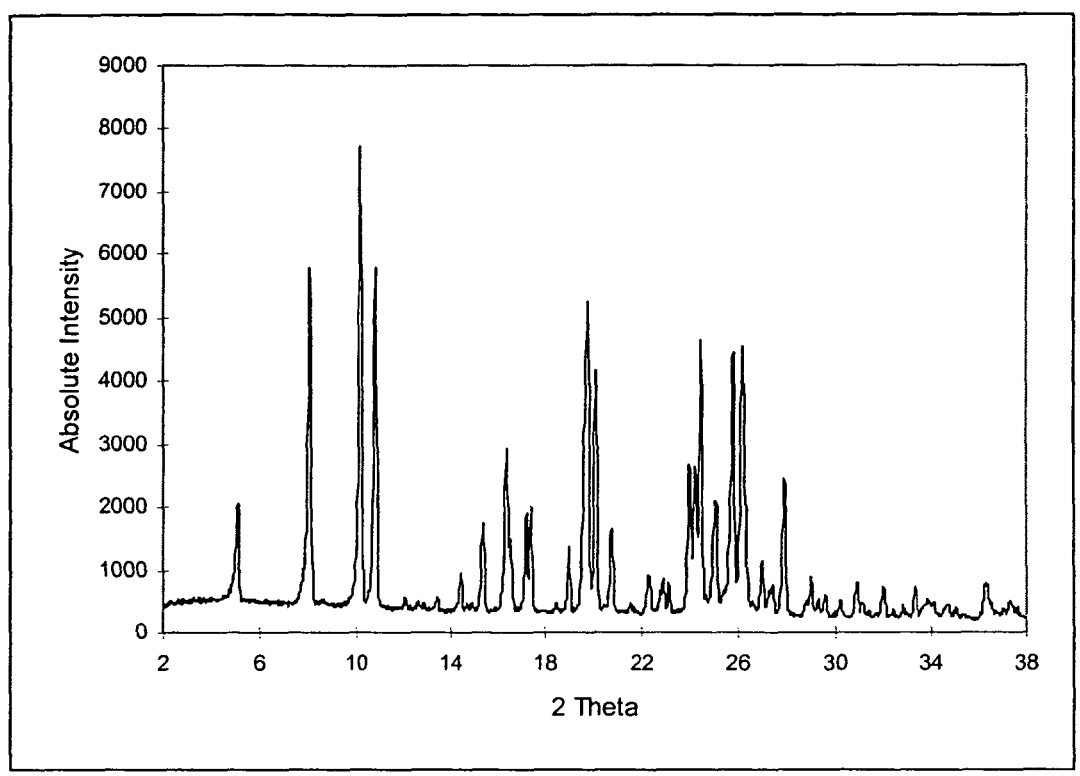

MEDICAMENTS CONTAINING VARDENAFIL HYDROCHLORIDE TRIHYDRATE

This application is a Continuation application of U.S. patent application Ser. No. 10/521,534 filed on Aug. 31, 2005, now U.S. Pat. No. 8,273,876, which patent is a 371 National Stage filing of PCT/EP03/07093 filed Jul. 3, 2003, which claims priority to German Patent Application No. 102 32 113.2 filed Jul. 16, 2002, the contents of each of which are incorporated herein by reference.

The application relates to medicaments which comprise vardenafil hydrochloride substantially as trihydrate in solid form, and processes for the production thereof.

The active pharmaceutical ingredient vardenafil (IUPAC name: 2-ethoxy-5-[(4-ethyl-1-piperazinyl)sulfonyl]phenyl}-5-methyl-7-propylimid-azo[5,1-f][1,2,4]triazin-4(3H)-one), vardenafil hydrochloride and vardenafil hydrochloride trihydrate and the use thereof from the treatment of erectile dysfunction is described in WO 99/24433 as Examples 19, 20 and 336.

It has been found that vardenafil hydrochloride occurs in four different polymorphic forms (anhydrous modifications I with melting point of 217° C., modification II with melting point of 190° C., modification III with melting point of 183-186° C., modification IV with transition point of 166° C.) and that none of these polymorphic forms is preferentially formed at room temperature. In addition, the individual polymorphic forms may take up different amounts of water, depending on the ambient humidity and temperature, and form with water further polymorphic forms, called pseudopolymorphic forms.

Since different polymorphic forms of a substance frequently differ in their dissolving behavior, these differences may become manifest for example in the bioavailability (AUC), maximum plasma concentration ($C_{max}$) and time of appearance of the maximum plasma concentration (AUC-max). It is also possible for absorption to be reduced, resulting in an inadequate or entirely absent effect.

Thus there is on the one hand the problem that solid medicaments must comprise the active ingredient vardenafil hydrochloride in defined and reproducible form. However, on the other hand, the polymorphic forms of vardenafil HCl cannot be prepared or isolated in pure form because they each take up small amounts of water and thus exist as mixture of the polymorphic form and of a hydrate.

For these reasons, vardenafil hydrochloride is unsuitable as ingredient of medicaments in which the active ingredient is to be present in solid form.

BRIEF DESCRIPTION OF THE FIGURES

FIG. 2 shows the Raman spectrum of vardenafil HCL 3 $H_2O$.

FIG. 3 shows the detection of the trihydrate form of vardenafil HCL in a 20 mg tablet.

FIG. 4 shows the IR spectrum of vardenafil HCL 3 $H_2O$.
FIG. 5 shows the NIR spectrum of vardenafil HCL 3 $H_2O$.
FIG. 6 shows the FIR spectrum of vardenafil HCL 3 $H_2O$.

FIG. 7 shows the $^{13}C$ solid NMR spectrum of vardenafil HCL 3 $H_2O$.

FIG. 8 shows the X-ray diffractogram of vardenafil HCL 3 $H_2O$.

DETAILED DESCRIPTION

Figure 1A:
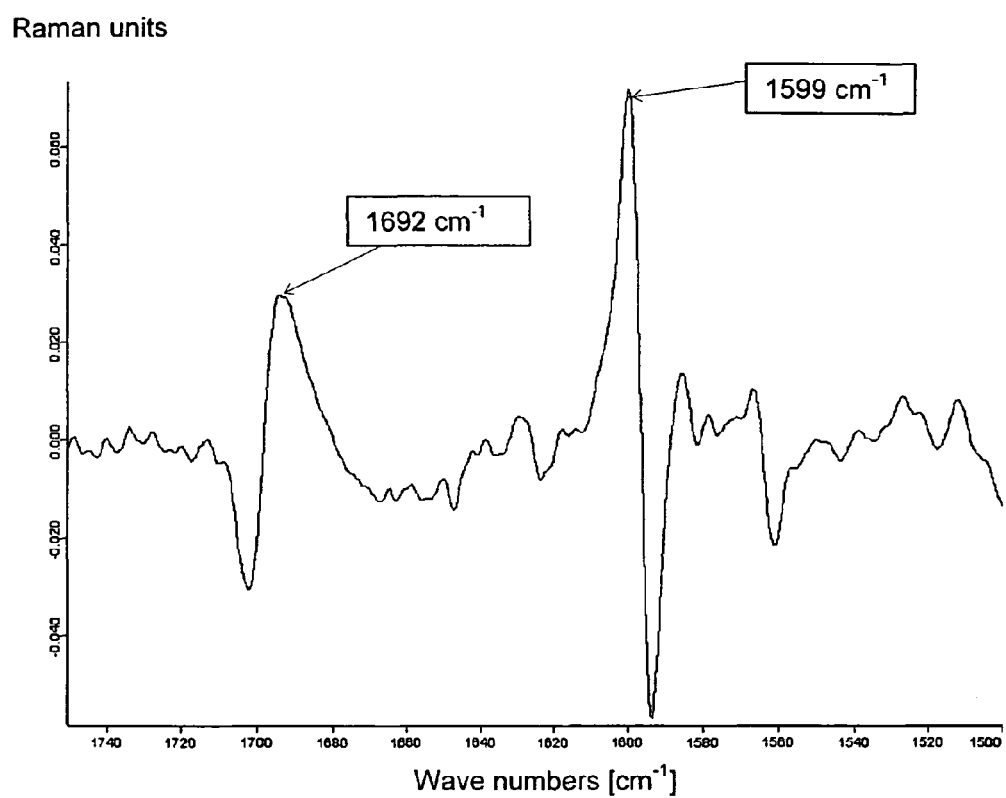
FIG. 1a shows the Raman difference spectrum (=spectrum of tablet–spectrum of vardenafil HCL 3 $H_2O$) of tablets of Example 6 before rehydration of vardenafil HCL anhydrous non-rehydrated tablets.

It has now been found that on use of vardenafil hydrochloride in the form of the trihydrate it is possible to obtain solid medicaments in uniform and reproducible form when these medicaments are moistened during or after their production.

The invention therefore relates to a process for producing medicaments comprising vardenafil hydrochloride trihydrate in solid form, characterized in that
  a) vardenafil hydrochloride with any content of water of crystallization is employed in the production of the medicament,
  b) the vardenafil hydrochloride is converted into the trihydrate form at an intermediate processing stage or in the final product, and
  c) where appropriate the process conditions in the following process steps are controlled so that the content of water of crystallization of the vardenafil hydrochloride trihydrate changes negligibly.

Vardenafil hydrochloride can be employed in this process with any water content, i.e. as trihydrate or in a form whose content of water of crystallization differs substantially from 9.3% by weight.

Vardenafil hydrochloride is converted into the trihydrate form in one of the next processing stages or in the final product and, where appropriate, the process conditions in the following process steps are controlled so that the content of water of crystallization of the vardenafil hydrochloride trihydrate does not change.

Conversion into the trihydrate form takes place according to the invention by bringing the intermediate processing stage or the final product into contact with moistened gas in a suitable system until there has been substantial formation of the trihydrate of vardenafil hydrochloride.

Moistened gas is, in particular, air with a relative humidity of from 35% to 100%, particularly preferably 50% to 99%. Suitable systems are all systems or chambers in which the moistened gas can be introduced or provided and brought into contact with the pharmaceutical forms as uniformly as possible, or in which the pharmaceutical forms can be incubated under the stated conditions. The time for which the moistened gas is passed over or in, or the residence time of the pharmaceutical form in the system and the relative humidity of the gas depends on the initial water content of the pharmaceutical form and the ratio of amounts between moistened gas and pharmaceutical form. It may vary from a few minutes up to several days, with 0.5-12 hours being sufficient in most cases. In the case of packaged pharmaceutical forms, generally times of 1 day-6 months are sufficient.

Solid medicaments are all pharmaceutical forms which comprise vardenafil hydrochloride trihydrate in solid form, such as powders, granules, tablets, film-coated tablets, sugar-coated tablets, fast-dissolving flakes or hard gelatin capsules.

Solid medicaments for the purposes of the invention are preferably tablets, especially coated tablets, because in the processing of vardenafil hydrochloride trihydrate to produce tablets, especially during coating of the tablets, by conventional methods there is to a particular extent partial or complete dehydration of the trihydrate again, and the active ingredient is again present non-uniformly in a plurality of polymorphic and pseudopolymorphic forms.

Besides vardenafil hydrochloride trihydrate, which exists at room temperature in only one crystalline modification (the water content in vardenafil hydrochloride trihydrate is 9.3% by weight), the medicaments product according to the invention comprise further pharmaceutical excipients known to the skilled worker.

The tablets of the invention comprise in addition to vardenafil hydrochloride trihydrate preferably fillers, disintegrants and lubricants and, where appropriate, further excipients. The tablets of the invention preferably comprise 0.1-70% by weight vardenafil hydrochloride trihydrate, 0.1-10% by weight disintegrant, 0.1-2% by weight lubricant and, where appropriate, further adjuncts, and the filler as remaining ingredients.

The tablet comprises preferably microcrystalline cellulose as filler, preferably crospovidone as disintegrant, preferably magnesium stearate as lubricant.

Further adjuncts which may be added where appropriate to the tablet are, by way of example and preferably, flow regulators such as colloidal silicon dioxide.

Particular preference is given to coated tablets which, also in the form ready for administration, comprise the active ingredient vardenafil hydrochloride reproducibly in the trihydrate modification.

Coated tablets are unambiguously defined by the European Pharmacopeia, 3rd edition 1997, page 1852: "Coated tablets are tablets covered with one or more layers of mixtures of various substances such as natural or synthetic resins, gums, gelatin, inactive and insoluble fillers, sugars, plasticizers, polyols, waxes, coloring matter authorized by the competent authority and sometimes flavoring substances and active substances. The substances used as coatings are usually applied as a solution or suspension under conditions in which evaporation of the solvent or dispersant occurs. When the coating is a very thin polymeric coating, the tablets are known as film-coated tablets."

Reference is additionally made to the definition of tablets in the European Pharmacopeia, 3rd edition 1997.

Since the aim during the process is to dry off the solvent or dispersant and form a film from the coating material, on production of coated tablets comprising vardenafil hydrochloride trihydrate by the conventional methods there is a particularly high degree of loss of water of crystallization from the active ingredient.

A preferred embodiment of the invention is therefore a method which produces coated vardenafil hydrochloride trihydrate tablets which comprise vardenafil hydrochloride reproducibly in the form of the trihydrate also in the form ready for administration.

In this preferred method, the coated vardenafil HCl tablets are subjected to a rehydration method. In this there is surprisingly formation in the coated tablet in all cases of one and the same trihydrate of vardenafil HCl, irrespective of which polymorphic form or mixture of polymorphic forms of vardenafil hydrochloride was initially present in the coated tablet.

A further aspect of the invention is therefore a method for producing coated tablets comprising vardenafil hydrochloride trihydrate, which is characterized in that coated tablets comprising vardenafil hydrochloride in any one or plurality of (hydrate) modifications and produced by conventional methods are subjected to a rehydration process.

The rehydration process is preferably carried out in such a way that the coated tablets are brought into contact in a suitable system with moistened gas until the trihydrate of vardenafil HCl has formed in the pharmaceutical form.

Suitable systems in which the rehydration process is carried out are, by way of example and preferably, in controlled environment cabinets, controlled environment rooms, fluidized bed granulators, coating apparatuses or drums.

Moistened gas is, by way of example and preferably, air with a relative humidity of from 35% to 100%, particularly preferably 50% to 99%.

During the rehydration step, the coated tablets may be at rest in the system, for example on the trays of a controlled environment cabinet or on the floor of a fluidized bed granulator or else be continuously or occasionally agitated for better mixing, for example in the drum or coating system. It is also possible to carry out the rehydration process after the coated tablets have been packaged in a pack which is permeable to water vapor. For this purpose, the packaged coated tablets are incubated in a controlled environment room.

The time the rehydration lasts depends on the initial water content of the coated tablet, the relative humidity of the moistened gas and the ratio of amounts between moist gas and the coated tablet. It may vary from a few minutes up to several days, and a rehydration time of 0.5-12 hours is sufficient in most cases. In the case of rehydration in a pack which is permeable to water vapor, the rehydration time additionally depends on the permeability to water vapor of the packaging material. In pharmaceutically customary blister packs, times of from 1 day up to 6 months are generally sufficient.

If the rehydration is carried out at an intermediate processing stage, the subsequent process conditions are controlled so that the content of water of crystallization of the vardenafil hydrochloride trihydrate does not change. For this purpose, the subsequent process steps are carried out at relative humidities of the air in contact with the product of 30-100%, preferably 35-99%.

It is astonishingly possible by the method of the invention to convert undefined vardenafil hydrochloride modification mixtures completely into the trihydrate form even in the dense structure of the finished coated tablet. There are moreover no unwanted side effects on the quality of the coated tablet, such as, for example, crumbling, cracking of coating layers or reduction in the rate of release of active ingredient.

It has also been found that the tablets produced by the method of the invention have a number of advantages over coated tablets produced using vardenafil hydrochloride trihydrate in conventional methods.

The application therefore also relates to the tablets produced by the method of the invention.

The advantage of the tablets of the invention or produced by the method of the invention is that the crystal structure of the active ingredient in the medicament is unambiguously defined, reproducible and stable over a wide range of relative humidities, corresponding coated tablets show faster disintegration and, contrary to the expectation from the prior art to date (David J. W. Grant, T. Higuchi, Techniques of Chemistry, Volume XXI, pages 38, 42 and 43), the rate of dissolution of the active ingredient from the tablets of the invention or produced by the method of the invention is constantly fast.

The tablets of the invention or produced by the method of the invention can be unambiguously defined on the basis of the crystal structure by the raman spectrum (the FT raman spectrum of vardenafil hydrochloride trihydrate shows a significant peak at 1701 cm$^{-1}$, Polymorphic and pseudopolymorphic forms with a lower water content and mixtures thereof by contrast have a band at 1692 cm$^{-1}$), IR spectrum, NIR spectrum, FIR spectrum, $^{13}$C solid NMR spectrum and the X-ray diffractogram (cf. FIGS. 2, 4-8 and Tab. 3-8 appended).

Concerning the production of vardenafil hydrochloride and vardenafil hydrochloride trihydrate, express reference is hereby made to the disclosure of WO 99/24433, in particular Examples 20 and 336.

The vardenafil hydrochloride in the medicaments is preferably at least 90 mol %, particularly preferably at least 95 mol %, in the trihydrate form.

The medicaments of the invention and the medicaments which can be produced by the method of the invention, especially the tablets of the invention or produced by the method of the invention, are suitable for the treatment and/or prophylaxis of diseases in humans and/or animals, in particular for the treatment of sexual dysfunctions, very especially for the treatment of erectile dysfunction.

The medicaments of the invention display several unexpected advantages: 1. The medicaments comprise vardenafil hydrochloride only in one crystalline modification. The medicaments can therefore be produced reproducibly, and they release of vardenafil at a reproducible and uniform rate. 2. The rate of release of the active ingredient from the medicaments of the invention is comparable to that from medicaments containing the solvate-free active ingredient. The rate of release from solvate-containing, in this case water-containing, crystals in the same solvent, in this case water, is usually less than from solvate-free crystals. 3. The disintegration time of the medicaments, especially the coated tablets, is shorter. The medicaments are therefore particularly suitable for the treatment of diseases for which the rapid onset of action is desired, such as, for example, for the treatment of erectile dysfunction. 4. In contrast to the highly hygroscopic medicaments containing solvate-free vardenafil hydrochloride, the medicaments of the invention are stable on storage for long periods and scarcely change their composition, in particular their water content.

The medicaments of the invention can be administered in various ways. Examples which may be mentioned are: oral, sublingual, buccal, nasal, inhalation, subcutaneous, or topical. Oral administration is preferred.

It has generally proved advantageous to administer amounts of about 0.001 to 10 mg/kg, on oral use preferably about 0.005 to 3 mg/kg, of body weight to achieve effective results.

It may nevertheless be necessary where appropriate to deviate from the stated amounts, in particular as a function of the body weight or the nature of the administration route, the individual response to the medicament, the nature of its formulation and the time or interval over which administration takes place. Thus, it may be sufficient in some cases to make do with less than the aforementioned minimum amount, whereas in other cases the stated upper limit must be exceeded. If larger amounts are administered, it may be advisable to distribute these in a plurality of single doses over the day.

The following examples serve to illustrate the invention further, but the invention is not confined to the examples.

EXAMPLES

Comparative Example 1 and Example 2

Tablets from the Conventional Production Methods of Drum Granulation and Coating and Improved Disintegration of Tablets of the Invention 216 g of microfine vardenafil HCl are mixed with 605 g of microcrystalline cellulose and 43.2 g of crospovidone. Addition of 2101 g of microcrystalline cellulose and 132 g of crospovidone is followed by mixing and subsequent mixing with 350 g of microcrystalline cellulose, 17.5 g of colloidal silicon dioxide and 35 g of magnesium stearate. The mixture is compressed in a rotary press to tablets with a diameter of 6 mm and a mass of 87 mg (equivalent to 5 mg of vardenafil base). In a coating apparatus, 43.5 mg of a coating suspension composed of 4.5% hypromellose, 1.5% macrogol 400, 1.23% titanium dioxide, 0.25% yellow iron oxide and 0.02% red iron oxide are sprayed on per tablet.

Comparative Example 1

Vardenafil hydrochloride is present in the tablets partly as trihydrate and as anhydrate (1 to 4 modifications). The tablets have a disintegration time of 2 minutes.

Example 2

The tablets are rehydrated in a fluidized bed granulator with 150 m$^3$/h inlet air of 30° C. and 19 g/kg water content for 4 hours (equivalent to 70% relative humidity). The modification of the vardenafil HCl in the tablet thus corresponds according to the invention to the trihydrate. The tablets now have a disintegration time of only ½ minute.

Example 3

Stability of Tablets Produced According to the Invention 28.4 kg of micronized vardenafil HCl trihydrate is mixed with 69.6 kg of microcrystalline cellulose and 5.16 kg of sieved crospovidone in a mechanical mixer. The mixture is mixed with 182 kg of microcrystalline cellulose and 9.84 kg of crospovidone in a container mixer and granulated by dry drum granulation. After admixture of 1.50 kg of colloidal silicon dioxide and 3.00 kg of magnesium stearate, tablets with a mass of 125 mg and a diameter of 7 mm are produced in a rotary tablet press. The uncoated tablets are coated with a suspension of 5.74 kg of hypromellose, 1.91 kg of macrogol 400, 1.57 kg of titanium dioxide, 319 g of yellow iron oxide, 25.5 g of red iron oxide and 118 kg of purified water in a commercially available coating system. The modification of vardenafil HCl in the coated tablets does not correspond to the trihydrate form and therefore represents an undefined mixture of anhydrous and hydrous forms of vardenafil HCl. The coated tablets are treated with air having a water content of 16 g of water/kg (corresponds to 80% relative humidity) in the coating system at 25° C. for 5 hours. The modification of vardenafil HCl in the rehydrated tablets corresponds to the trihydrate.

Stability test: The tablets with vardenafil HCl trihydrate are stored in the open at 25° C. and 30% relative humidity for one week. Despite the low humidity, no loss of water of crystallization occurs during this, and the vardenafil HCl active ingredient modification still corresponds to the trihydrate form.

Example 4

Active Ingredient Release from Tablets Produced According to the Invention 336 g of vardenafil HCl is mixed with 2216 g of microcrystalline cellulose and 134 g of crospovidone and granulated dry. Transfer of the granules is followed by mixing with 283 g of microcrystalline cellulose, 16 g of crospovidone and 15 g of magnesium stearate and compression to tablets with a diameter of 5 mm and a mass of 48 mg (equivalent to 5 mg of vardenafil base per tablet). The tablets are given a white coating with 57.4 g of hypromellose, 19.1 g of macrogol 4000 and 19.1 g of titanium dioxide and stored in the open at 25° C. and 80% relative humidity for 4 days. The modification of vardenafil HCl in the tablets corresponds to the trihydrate form.

As shown by the release data in Table 1, the tablets of the invention produced in this way show an extremely rapid release of active ingredient despite the complete restoration of the trihydrate form of vardenafil HCl in the finished tablet.

TABLE 1

Active ingredient release from tablets of Example 4

| Time | Active ingredient release |
|---|---|
| 5 min | 100% |
| 10 min | 101% |
| 30 min | 101% |
| 45 min | 101% |

Release conditions: n=6, USP paddle, 900 ml 0.1-M-HCl, 75 rpm, 10 .mu.m filter

Example 5

Small Variation in the Relative Bioavailability of Tablets of the Invention 0.645 kg of vardenafil HCl are mixed with 2.42 kg of microcrystalline cellulose and 161 of crospovidone, sieved and granulated dry with a drum. The granules are then mixed with 0.339 kg of microcrystalline cellulose, 18.8 g of crospovidone and 18 g of magnesium stearate and compressed to circular tablets with a diameter of 7 mm and a mass of 120 mg (equivalent to 20 mg of vardenafil base). The tablets are coated with 0.765 mg of macrogol 4000, 2.295 mg of hypromellose and 0.765 mg of titanium dioxide (amounts per tablet in each case). The trihydrate form of vardenafil HCl is produced in the finished tablets by exposing them on plates in a controlled environment room at 16-24° C. and 60-75% relative humidity for 72 hours.

For comparison purposes, a solution consisting of 21.49 mg of vardenafil HCl (equivalent to 20 mg of vardenafil base), 38.69 mg of methyl parahydroxybenzoate, 4.298 mg of propyl parahydroxybenzoate, 6448 mg of sucrose, 17419 mg of water and lactic acid ad pH 3.9 is produced. The pharmacokinetics after administration of tablets and solution were compared in a randomized, open crossover study on 12 male subjects (Table 2).

TABLE 2

Pharmacokinetic parameters after administration of tablets of Example 5 and a solution (geometric means/geometric standard deviations)

| Parameter | Tablets corr. to Example 5 | Comparative solution |
|---|---|---|
| AUC (µg × h/L) | 60.2/1.64 | 64.6/1.78 |
| Cmax (µg/L) | 21.1/1.86 | 22.5/2.09 |

The results show that tablets of the invention have a relative bioavailability of 93% compared with an aqueous solution. Since the geometric standard deviations of the bioavailability and maximum plasma concentration are less than after administration of the aqueous solution, it is possible to rule out variations resulting from variable polymorphic or pseudopolymorphic forms of vardenafil HCl in solid form in the tablet.

Example 6

0.871 kg of vardenafil HCl trihydrate, 2.13 kg of microcrystalline cellulose and 0.158 kg of sieved crospovidone are vigorously mixed in a plowshare mixer. This mixture is mixed with 3.08 kg of microcrystalline cellulose and 0.167 kg of crospovidone, drum-granulated and then mixed with 0.0325 kg of colloidal silicon dioxide and 0.0650 kg of magnesium stearate.

The mixture is tableted in a rotary press to tablets with a diameter of 8 mm and a mass of 177 mg (equivalent to 20 mg of vardenafil base) and coated with 2.76 kg of an aqueous coating suspension with 4.5% hypromellose, 1.5% macrogol 400, 1.23% titanium dioxide, 0.25% yellow iron oxide and 0.02% red iron oxide in a coating pan. The modification of vardenafil HCl in the tablets does not correspond to the trihydrate form (FIG. 1a).

The rehydration is carried out by introducing the coated tablets into a Glatt GPCG 1/3 type fluidized bed granulator and treating with 150 m$^3$/h inlet air of 25° C. and 16 g/kg humidity (equivalent to 80% relative humidity) for 4 hours. The modification of vardenafil HCl in the tablets treated in this way corresponds to the trihydrate form (FIG. 1b).

FIG. 1a shows the Raman difference spectrum (=spectrum of tablet–spectrum of vardenafil HCL 3 H$_2$O) of tablets of Example 6 before rehydration of vardenafil HCL anhydrous non-rehydrated tablets.

Figure 1B:
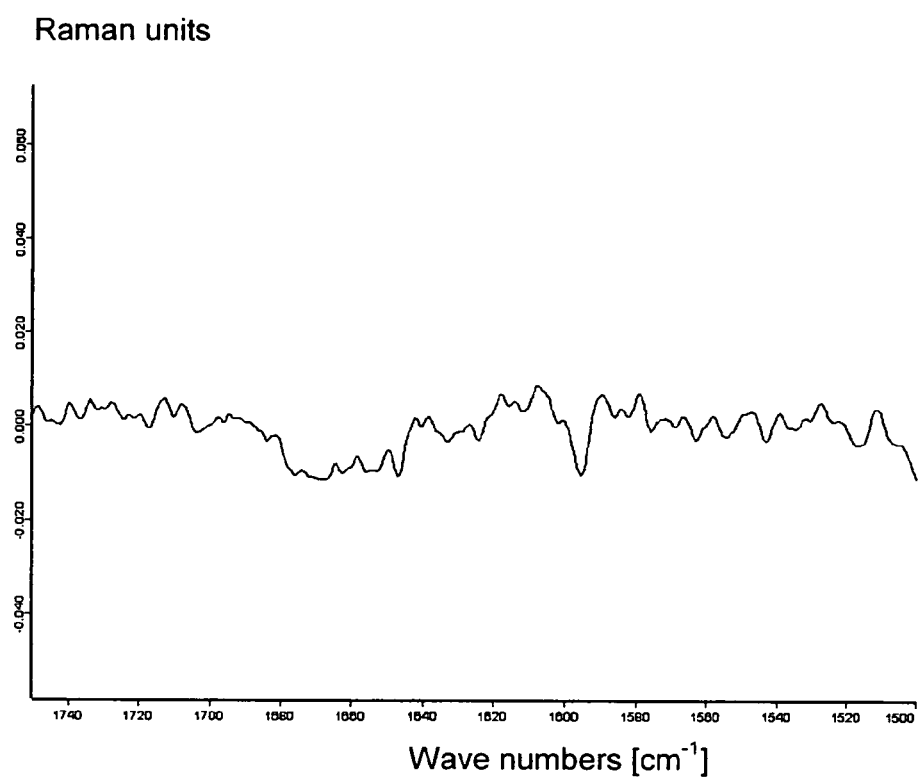
FIG. 1b shows the Raman difference spectrum (=spectrum of tablet–spectrum of vardenafil HCL 3 $H_2O$) of tablets of Example 6 after rehydration of vardenafil HCL anhydrous non-rehydrated tablets.

FIG. 1b shows the Raman difference spectrum (=spectrum of tablet–spectrum of vardenafil HCL 3 H$_2$O) of tablets of Example 6 after rehydration of vardenafil HCL anhydrous non-rehydrated tablets.

Example 7

37 kg of coated tablets produced as in Example 6 are treated after the coating in a tablet drum with 40 m$^3$/h inlet air at 21° C. and 84% relative humidity through a gas-introduction pipe for 3 days.

Example 8

12.3 kg of vardenafil HCl trihydrate, 30.2 kg of microcrystalline cellulose and 2.24 kg of sieved crospovidone are mixed. This mixture is mixed with a further 238 kg of microcrystalline cellulose and 12.8 kg of sieved crospovidone, drum-granulated and then mixed with 1.5 kg of colloidal silicon dioxide and 3.0 kg of sieved magnesium stearate. This mixture is compressed in a rotary tablet press to circular tablets with a diameter of 5.5 mm and a mass of 72 mg. The tablets are given a red coating with 5.74 kg of hypromellose, 1.91 kg of macrogol 400, 1.57 kg of titanium dioxide, 319 g of yellow iron oxide and 25.5 g of red iron oxide. The coated tablets are rehydrated in two part-batches of about 140 kg by treating them in a Glatt 1250 type coating system with 2000 m$^3$/h inlet air of 16 g humidity/kg at 25° C. (equivalent to 80% relative humidity) for 5 hours.

Example 9

600 g of tablets consisting of 5.926 mg of vardenafil HCl trihydrate, 4.35 mg of crospovidone, 0.87 mg of magnesium stearate, 75.419 mg of microcrystalline cellulose and 0.435 mg of colloidal silicon dioxide are coated in a Kugelcoater with an organic coating solution consisting of 6.65% cellulose acetate, 0.35% PEG 3350, 92.535% acetone and 0.465% water until 82.76 g of coating has been applied. The coated tablets are treated on trays at 25° C./80% relative humidity for 24 hours.

Example 10

Tablets are produced as described Example 6. After coating, the tablets are sealed into blister packs which consist of 20 μm aluminum sheet combined with 3.5 g/m² PP sheet, and 300 μm colorless and transparent PP sheet. The blister packs are incubated under controlled conditions at 25° C. and 60% relative humidity for six months. The modification of vardenafil HCl in the tablets treated in this way corresponds to the trihydrate form.

Example 11

2.96 kg of vardenafil hydrochloride trihydrate, 7.25 kg of microcrystalline cellulose and 538 g of crospovidone are mixed in a plowshare mixer. The mixture is mixed in a freefall mixer with 26.1 kg of microcrystalline cellulose and 1.64 kg of crospovidone. The mixture is granulated dry in a drum granulator and then mixed with 4.35 kg of microcrystalline cellulose, 218 g of colloidal silicon dioxide and 435 g of magnesium stearate. This mixture is compressed in a tablet press to circular tablets with diameter of 6 mm. The tablets are coated in a coating pan with a coating dispersion which has the following ingredients: 832 g of hypromellose, 277 g of macrogol 400, 227 g of titanium dioxide, 17.1 kg of water, 46.2 g yellow and 3.70 g of red iron oxide.

The finished tablets are sealed in blister packs which were produced using a 300 μm colorless and transparent PP sheet and 20 μm aluminum sheet with sealing layer. In this state, the modification of vardenafil HCl does not correspond to the trihydrate form. The blister packs are then incubated at 25° C. and 80% humidity for three days. The active ingredient in the tablet then corresponds to vardenafil hydrochloride trihydrate.

Example 12

The presence of the trihydrate form of vardenafil HCl in the finished coated tablet is investigated by FT raman spectroscopy. The FT raman spectrum of vardenafil HCl trihydrate tablets is distinguished in contrast to corresponding placebo tablets by bands at 1701 cm$^{-1}$, 1624 cm$^{-1}$, 1594 cm$^{-1}$, 1580 cm$^{-1}$, 1561 cm$^{-1}$, and 1518 cm$^{-1}$ (FIG. 2). Unambiguous assignment of these bands to the active ingredient vardenafil HCl trihydrate is proved as follows. A single-crystal X-ray structural analysis of vardenafil HCl trihydrate exists, and the theoretical two-dimensional X-ray powder diffractogram is calculated with the aid thereof. If the X-ray powder diffractogram obtained experimentally for a given sample of the active ingredient agrees with the theoretical diffractogram, then the given sample is unambiguously vardenafil HCl trihydrate. The FT raman spectrum of the same sample is thus unambiguously to be assigned to vardenafil HCl trihydrate (Tab. 3). If this substance is dried, bands of 1 to 4 anhydrate modifications appear in the FT raman spectrum, e.g. at about 1692 cm$^{-1}$ and 1599 cm$^{-1}$. The intensity of the bands belonging to vardenafil HCl trihydrate in the FT raman spectrum is reduced according to the amount remaining in the sample (FIG. 3). Absence of the bands at about 1692 cm$^{-1}$ and 1599 cm$^{-1}$ in the FT raman spectrum can thus be used to test for complete rehydration of vardenafil HCl trihydrate. The practical procedure for this is as follows: the FT raman spectrum of vardenafil HCl trihydrate and the FT raman spectrum of the active ingredient-free tablet of the corresponding formulation is subtracted from the FT raman spectrum of a given tablet. Remaining raman intensities which are larger than the spectral noise and >0 are bands of components other than those present in the active ingredient-free tablet and vardenafil HCl trihydrate. In the case of vardenafil HCl tablets these are, for example, bands of 1 to 4 anhydrate modifications of vardenafil HCl.

FIG. 2: shows the Raman spectrum of vardenafil HCL 3 H$_2$O.

TABLE 3

Table of bands in the raman spectrum of vardenafil HCl 3 H$_2$O Peak [cm$^{-1}$]

| |
|---|
| 197 |
| 260 |
| 297 |
| 313 |
| 390 |
| 460 |
| 499 |
| 583 |
| 624 |
| 649 |
| 733 |
| 746 |
| 778 |
| 817 |
| 882 |
| 927 |
| 1045 |
| 1089 |
| 1110 |
| 1167 |
| 1216 |
| 1224 |
| 1236 |
| 1253 |
| 1281 |
| 1306 |
| 1326 |
| 1357 |
| 1381 |
| 1395 |
| 1424 |
| 1456 |
| 1517 |
| 1561 |
| 1581 |
| 1594 |
| 1623 |
| 1701 |
| 2940 |
| 2983 |
| 3002 |

FIG. 3: shows the detection of the trihydrate form of vardenafil HCL in a 20 mg tablet.

FIG. 4: shows the IR spectrum of vardenafil HCL 3 H$_2$O.

TABLE 4

Table of bands in the IR spectrum of vardenafil HCl 3 H$_2$O Peak [cm$^{-1}$]

| |
|---|
| 515 |
| 560 |
| 583 |
| 604 |
| 648 |
| 663 |
| 684 |
| 697 |

TABLE 4-continued

Table of bands in the IR spectrum of vardenafil HCl 3 H$_2$O
Peak [cm$^{-1}$]

| |
|---|
| 714 |
| 721 |
| 732 |
| 745 |
| 751 |
| 820 |
| 841 |
| 882 |
| 906 |
| 927 |
| 954 |
| 983 |
| 1026 |
| 1043 |
| 1074 |
| 1089 |
| 1108 |
| 1132 |
| 1153 |
| 1168 |
| 1182 |
| 1202 |
| 1226 |
| 1236 |
| 1253 |
| 1264 |
| 1289 |
| 1339 |
| 1357 |
| 1382 |
| 1388 |
| 1395 |
| 1411 |
| 1421 |
| 1454 |
| 1475 |
| 1517 |
| 1580 |
| 1594 |
| 1623 |
| 1707 |
| 1935 |
| 2478 |
| 2517 |
| 2544 |
| 2621 |
| 2641 |
| 2680 |
| 2722 |
| 2875 |
| 2934 |
| 2967 |
| 3068 |
| 3332 |
| 3467 |

FIG. 5: shows the NIR spectrum of vardenafil HCL 3 H$_2$O.

TABLE 5

Table of bands in the NIR spectrum of vardenafil HCl 3 H$_2$O Peak
Peak [cm$^{-1}$]

| |
|---|
| 4041 |
| 4083 |
| 4165 |
| 4192 |
| 4266 |
| 4353 |
| 4428 |
| 4556 |
| 4655 |
| 4744 |
| 4804 |
| 5107 |

TABLE 5-continued

Table of bands in the NIR spectrum of vardenafil HCl 3 H$_2$O Peak
Peak [cm$^{-1}$]

| |
|---|
| 5694 |
| 5833 |
| 5911 |
| 6080 |
| 6501 |
| 6818 |
| 8479 |

FIG. 6: shows the FIR spectrum of vardenafil HCL 3 H$_2$O.

TABLE 6

Table of bands in the FIR spectrum of vardenafil HCl 3 H$_2$O
Peak [cm$^{-1}$]

| |
|---|
| 82 |
| 102 |
| 115 |
| 154 |
| 243 |
| 259 |
| 297 |
| 315 |
| 326 |
| 345 |
| 384 |
| 426 |
| 434 |
| 460 |
| 481 |

FIG. 7 shows the $^{13}$C solid NMR spectrum of vardenafil HCL 3 H$_2$O.

TABLE 7

Table of bands in the .sup.13C solid NMR
spectrum of vardenafil HCl 3 H$_2$O
Peak [ppm]

| |
|---|
| 10.6 |
| 13.3 |
| 15.4 |
| 15.7 |
| 21.7 |
| 28.7 |
| 31.3 |
| 42.6 |
| 44.1 |
| 50.2 |
| 52.8 |
| 67.7 |
| 112.3 |
| 115.0 |
| 130.8 |
| 132.6 |
| 138.8 |
| 143.3 |
| 145.3 |
| 152.1 |
| 160.2 |

FIG. 8 shows the X-ray diffractogram of vardenafil HCL 3 H$_2$O.

TABLE 8

List of peaks in the X-ray diffractogram of vardenafil HCl 3 H$_2$O
Peak [2 Theta]

| |
|---|
| 5.1 |
| 8.1 |

TABLE 8-continued

List of peaks in the X-ray diffractogram of vardenafil HCl 3 H$_2$O
Peak [2 Theta]

10.2
10.8
14.4
15.3
16.3
17.2
17.4
19.0
19.7
20.1
20.7
22.3
22.9
23.2
24.0
24.3
24.5
25.1
25.8
26.2
27.0
27.9
29.0
30.9
32.0
33.3

The invention claimed is:

1. A coated tablet comprising 0.1-70% by weight vardenafil hydrochloride, primarily in the form of vardenafil hydrochloride trihydrate, 0.1-10% by weight disintegrant, 0.1-2% by weight lubricant, and fillers as remaining ingredients, characterized in that the vardenafil hydrochloride trihydrate content of the vardenafil hydrochloride is at least 90 mol %.

2. A coated tablet as claimed in claim 1 comprising microcrystalline cellulose as filler.

3. A coated tablet as claimed in claim 1 comprising crospovidone as disintegrant.

4. A coated tablet as claimed in claim 1 comprising magnesium stearate as lubricant.

5. A coated tablet as claimed in claim 1 comprising microcrystalline cellulose as filler, crospovidone as disintegrant and magnesium stearate as lubricant.

6. A coated tablet as claimed in claim 1 comprising 4% by weight vardenafil hydrochloride trihydrate.

7. A coated tablet as claimed in claim 1 comprising 7% by weight vardenafil hydrochloride trihydrate.

8. A coated tablet as claimed in claim 1 comprising 9% by weight vardenafil hydrochloride trihydrate.

9. A coated tablet as claimed in claim 1 comprising 13% by weight vardenafil hydrochloride trihydrate.

10. A coated tablet as claimed in claim 1 comprising 5% by weight crospovidone.

11. A coated tablet as claimed in claim 1 comprising 1% by weight magnesium stearate.

12. A coated tablet as claimed in claim 1 comprising microcrystalline cellulose as filler, crospovidone as disintegrant, magnesium stearate as lubricant and 4% by weight vardenafil hydrochloride trihydrate.

13. A coated tablet as claimed in claim 1 comprising microcrystalline cellulose as filler, crospovidone as disintegrant, magnesium stearate as lubricant and 7% by weight vardenafil hydrochloride trihydrate.

14. A coated tablet as claimed in claim 1 comprising microcrystalline cellulose as filler, crospovidone as disintegrant, magnesium stearate as lubricant and 9% by weight vardenafil hydrochloride trihydrate.

15. A coated tablet as claimed in claim 1 comprising microcrystalline cellulose as filler, crospovidone as disintegrant, magnesium stearate as lubricant and 13% by weight vardenafil hydrochloride trihydrate.

* * * * *